(12) United States Patent
Rozema et al.

(10) Patent No.: US 7,348,453 B2
(45) Date of Patent: Mar. 25, 2008

(54) LABILE LINKAGE FOR COMPOUND DELIVERY TO A CELL

(75) Inventors: David B. Rozema, Madison, WI (US); Darren Wakefield, Fitchburg, WI (US)

(73) Assignee: Mirus Bio Corporation, Madison, WI (US)

( * ) Notice: Subject to any disclaimer, the term of this patent is extended or adjusted under 35 U.S.C. 154(b) by 490 days.

(21) Appl. No.: 10/929,707

(22) Filed: Aug. 30, 2004

(65) Prior Publication Data
US 2005/0054604 A1 Mar. 10, 2005

Related U.S. Application Data

(60) Provisional application No. 60/500,213, filed on Sep. 4, 2003.

(51) Int. Cl.
*C07C 65/21* (2006.01)
*A61K 47/18* (2006.01)

(52) U.S. Cl. ............... 562/473; 424/194.1; 424/179.1; 562/459; 562/471

(58) Field of Classification Search ............... 562/473, 562/471, 459; 424/179.1, 194.1; 514/1, 514/2
See application file for complete search history.

(56) References Cited

U.S. PATENT DOCUMENTS

| 4,946,931 | A | 8/1990 | Heller et al. |
| 4,957,998 | A | 9/1990 | Heller et al. |
| 6,414,001 | B2 | 7/2002 | Tomiyama et al. |

OTHER PUBLICATIONS

Adami RC et al. "Metabolic stability of glutaraldehyde cross-linked peptide DNA condensates." J Pharm Sci. 1999 vol. 88 No. 8 pp. 739-746.
Boussif O et al. "A versatile vector for gene and oligonucleotide transfer into cells in culture and in vivo: polyethylenimine." Proc Natl Acad Sci U S A. 1995 vol. 92 No. 16 pp. 7297-7301.
Capon B ".Intramolecular Catalysis in Glycoside Hydrolysis" Tetrahedron Letters, 1963 vol. 4 pp. 911-913.
Cheung CY et al. "A pH-sensitive polymer that enhances cationic lipid-mediated gene transfer." Bioconjug Chem; 2001 vol. 12 No. 6 pp. 906-910.
Danko et al. "High expression of naked plasmid DNA in muscles of young rodents." Hum. Mol. Genetics 1997 vol. 6 pp. 1435.
Dunn et al. "Steric and electronic effects on the neighboring general acid catalyzed hydrolysis of methyl phenyl acetals of formaldehyde." JACS 1970 vol. 92 pp. 2410-2416.
Fife et al. "Intramolecular carboxyl group participation in acetal hydrolysis." JACS 1971 vol. 93 pp. 6610-6614.
Godwin A et al. "New strategies for polymer development in pharmaceutical science—a short review." J Pharm Pharmacol 2001 vol. 53 No. 9 pp. 1175-1184.

Hu Z et al. "Characterization of norfloxacine release from tablet coated with a new pH-sensitive polymer, P-4135F." J Drug Target 1999 vol. 7 No. 3 pp. 223-232.
Jain R et al. "Controlled drug delivery by biodegradable poly(ester) devices: different preparative approaches." Drug Dev Ind Pharm 1998 vol. 24 No. 8 pp. 703-727.
Kamata H et al. "Amphiphilic peptides enhance the efficiency of liposome-mediated DNA transfection." Nucleic Acids Res. 1994 vol. 22 pp. 536-537.
Lai et al. "Acid-and Calcium-induced structural changed in phosphatidylethanolamine membranes stabilized by cholesteryl hemisuccinate" Biochemistry 1985 vol. 24 p. 1654-1661.
Lowman AM et al. "Oral delivery of insulin using pH-responsive complexation gels." J Pharm Sci 1999 vol. 88 No. 9 pp. 933-937.
Mechtler K et al "Gene transfer mediated by influenze virus peptides: the role of peptide sequences" New J. Chem. 1997 vol. 21 pp. 105-111.
Metrikin DC et al. "Intravitreal drug administration with depot devices." Curr Opin Ophthalmol 1994 vol. 5 No. 3 pp. 21-29.
Meyer O et al. "Copolymers of N-isopropylacrylamide can trigger pH sensitivity to stable liposomes." FEBS Lett 1998 vol. 421 No. 1 pp. 61-64.
Murthy N et al. "The design and synthesis of polymers for eukaryotic membrane disruption." J Control Release. 1999 vol. 61 No. 1-2 pp. 137-143.
Ohmori N et al. "The enhancing effect of anionic alpha-helical peptide on cationic peptide-mediating transfection systems." Biochem Biophys Res Commun. 1997 vol. 235 No. 3 pp. 726-729.
Pastan I et al. "Pseudomonas exotoxin: chimeric toxins." J Biol Chem. 1989 vol. 264 No. 26 pp. 15157-15160.
Plank C et al. "Application of membrane-active peptides for drug and gene delivery across cellular membranes." Adv Drug Deliv Rev 1998 vol. 34 No. 1 pp. 21-35.
Potineni A et al. "Poly(ethylene oxide)-modified poly(beta-amino ester) nanoparticles as a pH-sensitive biodegradable system for paclitaxel delivery." J Control Release 2003 vol. 86 No. 2-3 pp. 223-234.
Sezaki H et al. "Soluble macromolecular carriers for the delivery of antitumour drugs." Adv Drug Deliv Rev 1989 vol. 3 No. 2 pp. 247-266.
Wagner E et al. "Delivery of drugs, proteins and genes into cells using transferrin as a ligand for receptor-mediated endocytosis." Adv Drug Deliv Rev 1994 vol. 14 pp. 113-135.
Wagner E et al. "Influenza virus hemagglutinin HA-2 N-terminal fusogenic peptides augment gene transfer by transferrin-polylysine-DNA complexes: toward a synthetic virus-like gene-transfer vehicle." Proc Natl Acad Sci U S A. 1992 vol. 89 No. 17 pp. 7934-7938.
Wolff JA et al. "Direct gene transfer into mouse muscle in vivo." Science 1990 vol. 247 pp. 1465-1468.
Zuber et al. "Towards synthetic viruses" Adv Drug Deliv Rev. 2001 vol. 52 p. 245-253.

*Primary Examiner*—Charanjit S. Aulakh
(74) *Attorney, Agent, or Firm*—Mark K. Johnson; Kirk Ekena

(57) ABSTRACT

Described are ortho carboxy phenol derived acetals and compositions containing ortho carboxy phenol derived acetals which are useful for delivering biologically active compounds to cells. The acetals can be used to reversibly link up to three different molecules and have rapid hydrolysis kinetics in conditions which are present in a cell as well as in vivo. Cleavage of the acetal enhances delivery of the biologically active compound.

7 Claims, 2 Drawing Sheets where Pr is a protecting group
such as benzyl or acetal

LABILE LINKAGE FOR COMPOUND DELIVERY TO A CELL

CROSS-REFERENCE TO RELATED APPLICATIONS

This application claims the benefit of U.S. Provisional Application No. 60/500,213, filed Sep. 4, 2003.

BACKGROUND OF THE INVENTION

The route of cellular entry for most conventional drugs is diffusion across the biological membrane. For this reason, drugs tend to be small (MW<500) and amphipathic, containing both hydrophobic and hydrophilic functionalities. These characteristics engender molecules with water solubility, while allowing them to cross the nonpolar lipid bilayer of the cell membrane. However, many potential drugs, including those used in gene therapy are too hydrophilic and/or too large to be delivered to cells by diffusion across a cell membrane. For this reason, a major barrier to gene therapy is the delivery of the large hydrophilic drugs to the cellular cytoplasm or nucleus.

The route of entry into cells for most membrane impermeable molecules is endocytosis. After internalization, the contents of an endosome are typically recycled back to the cell surface or delivered to another intracellular membrane bound vesicle, such as a lysosome. Delivery to a lysosome occurs concomitantly with a drop in pH of the vesicle interior, from pH about 7.5 outside the cell, to pH 7-6 in early and late endosomes, to pH about 5 or less in lysosomes. To deliver endocytosed membrane impermeable molecules to the cell cytoplasm, the molecule must therefore be co-delivered with compounds that facilitate release of the molecule from an internal membrane bound vesicle or facilitate membrane permeability of the molecule.

Release of endosomal contents can occur through disruption of the vesicle membrane or rupture of the vesicle. Agents used to accomplish endosomal release include compounds which are proposed to act as proton sponges and membrane active compounds that directly disrupt membrane structure. These compounds, e.g., adenoviral coat proteins, often rely upon the environment of the endosome/lysosome to trigger their activation. For example, these compounds may be substrates for lysosomal degradative enzymes such as proteases, nucleases and glycosylases. Proteolysis can result a activation of a membrane active compound which then destabilizes the bilayer.

The drop in pH as an endosome matures into a lysosome may also be utilized to trigger membrane disruption and content release. pH-sensitive compounds, including polymers and lipids, have found broad application in the area of drug delivery.

Agents that are weakly basic, $pK_a$ 5-7, can be reversibly protonated in the acidic environment of the endosome. Examples include chloroquine, polyethyleneimine, and histidylated poly-L-lysine. The effect of these buffering compounds is to increase the number of protons required for a drop in pH. It is postulated that the increased number of protons, and as a consequence their counterions, causes an increase in the osmotic pressure of the endosome that leads to membrane rupture, the proton sponge effect.

Another mechanism for pH-dependent membrane disruption is the use of agents whose interaction with a membrane is dependent upon protonation, e.g. cholesterol hemisuccinate, viral coat peptides and their derivatives, and polypropylacrylic acid (PPA). A common characteristic of these agents is that they are carboxylic acid- and hydrophobic group-containing molecules that become less charged as the pH drops. The decrease in charge renders the molecules more hydrophobic, and thus more membrane disruptive.

Still other compounds rely on pH dependent cleavage events to facilitate membrane disruptive activation, prodrug activation, or drug release. pH-sensitive polymers have found broad application in the area of drug delivery, exploiting various physiological and intracellular pH gradients for the purpose of controlled or targeted release of drugs (both low molecular weight conventional drugs as well as membrane impermeable biologically active compounds). The controlled release of pharmaceuticals after their administration is under intensive development. pH sensitivity can be broadly defined as any change in polymer's physico-chemical properties over certain range of pH. A more narrow definition demands significant changes in a compound's or polymer's interaction with biological components or its ability to retain (release) a bioactive substance (drug) in a physiologically tolerated pH range (usually pH 5.5-8).

Drugs may be administered to a patient in an inactive form, a called a prodrug. The prodrug is converted into the biologically active compound upon interaction with specific enzymes in the body or upon exposure to specific environments in the body. For example, anticancer drugs are quite toxic and are administered as prodrugs which do not become active until they come in contact with the cancerous cell (Sezaki et. al. 1989). Studies have found that the pH in solid tumors is 0.5 to 1 unit lower than in normal tissue and the use of pH-sensitive polymers for targeting tumors has been shown in vitro (Potineni et al 2003). pH-sensitive polymers have also been used in conjunction with liposomes for the triggered release of an encapsulated drug. For example, hydrophobically-modified N-isopropylacrylamide-methacrylic acid copolymer can render regular egg phosphatidyl chloline liposomes pH-sensitive by pH-dependent interaction of grafted aliphatic chains with lipid bilayer (Meyer et al. 1998).

Polyions can be divided into three categories based on their ability to donate or accept protons in aqueous solutions: polyacids, polybases and polyampholytes. Polybases (polycations) have found broad applications as transfection agents for nucleic acid delivery applications due to the fact they readily interact with polyacids (i.e., nucleic acid). An example is polyethyleneimine (PEI). This polymer facilitates nucleic acid condensation, and electrostatic adsorption on the cell surface followed by endocytosis. Subsequent endosomal release of the nucleic acid is proposed to occur though the so-called proton sponge effect.

Polycations can facilitate DNA condensation. The volume which one DNA molecule occupies in a complex with polycations is lower than the volume of the free DNA molecule. A significant number of multivalent cations with widely different molecular structures have been shown to induce condensation of DNA. Multivalent cations with a charge of three or higher have been shown to condense DNA. Analysis has shown DNA condensation to be favored when 90% or more of the charges along the sugar-phosphate backbone are neutralized. The electrophoretic mobility of nucleic acid-polycation complexes can change from negative to positive in excess of polycation.

The size of a DNA/polymer complex is important for gene delivery in vivo. In terms of intravenous injection, the polynucleotide-containing complex needs to be able to cross the endothelial barrier and reach the parenchymal cells of interest. The largest endothelia fenestrae (holes in the endothelial barrier) occur in the liver and have an average diameter of 100 nm under normal conditions. In other organs, the endothelium can be described as a structure that has a large number of small pores with a radius of 4 nm and a low number of larger pores with a radius of 20-30 nm. The size of the DNA complexes is also important for the cellular uptake process. Since endocytic vesicles typically have an internal diameter of about 100 nm, complexes smaller than about 100 nm in diameter are preferred.

Depending upon conditions used to condense polynucleotide, three main types of structures can be formed: toroidal structures containing as little as a single polynucleotide molecule, microaggregates that remain in suspension and can be toroids, rods or small aggregates, and large aggregates that sediment readily.

A polycation also can form a cross-bridge between an anionic polynucleotide and the anionic surface of a cell. As a result the main mechanism of polynucleotide/polycation complex translocation to the intracellular space may be non-specific adsorptive endocytosis. Polycations are furthermore a convenient linker for attaching functional groups. Polymer/polynucleotide complexes can also protect the polynucleotide against nuclease degradation.

Optimal transfection activity in vitro and in vivo can require an excess of polycation molecules. However, the presence of excess polycations may be toxic to cells and tissues. Moreover, the non-specific binding of cationic particles to all cells interferes with cell type specific targeting. Positive charge also has an adverse influence on biodistribution of the complexes in vivo.

Several modifications of DNA/cation particles have been created to circumvent the nonspecific interactions of the DNA/cation particle and the toxicity of cationic particles. Examples of these modifications include attachment of steric stabilizers. Another example is recharging the DNA particle by the addition of polyanions which interact with the cationic particle, thereby lowering its surface charge, i.e. recharging of the DNA particle (U.S. application Ser. No. 09/328,975). Another example is cross-linking the polymers and thereby caging the complex (U.S. application Ser. Nos. 08/778,657, 09/000,692, 9/724,089, 09/070,299, and 09/464,871).

Linkages that are rapidly cleavable or reversible under specific environments, such as the reduced pH of an intracellular endosome/lysosome or tumor, are useful in developing deliver vectors for a variety of biologically active compounds. The acetal linkage has been used extensively as an acid-labile bond in the delivery of drugs. The acetal bond has been used in the construction of drug carriers and to link drug with carriers. Acetals have also been used to construct acid-cleavable surfactants, to separate the detergent into hydrophobic tail and hydrophilic head group. However, acetal linkages created to date have half-lives of hours to days in aqueous conditions at pH 4-7. Acetals which cleave at faster rates would make better linkages agents in certain applications.

SUMMARY OF THE INVENTION

Compounds and methods are described for enhancing the delivery of a biologically active compound to a cell. In a preferred embodiment, the compounds comprise acid labile ortho carboxy phenol derived acetals. The acetals can be used to reversibly link up to three different molecules which are rapidly cleaved from each other upon exposure to an acidic pH environment.

In a preferred embodiment, the described ortho carboxy phenol derived acetals may be used to form acid cleavable transfection agents. The transfection agent can be a compound which is non-covalently associated with a biologically active compound to be delivered to a cell. Alternatively, the transfection agent can be a compound which is covalently linked to a biologically active compound. Cleavage of the transfection agent can release either a non-covalently associated or covalently linked biologically active compound from the transfection agent. The transfection agent may be designed such that cleavage of the transfection agent increases membrane activity of the agent.

In a preferred embodiment, we describe a composition for delivering a biologically active compound to a cell comprising: the biologically active compound electrostatically associated with a pH sensitive ortho carboxy acetal containing delivery agent to form a complex. For delivery of a polynucleotide, a preferred delivery agent is a polycation or a lipid. The ortho carboxy acetal may be present in a polymer or lipid prior to association of the polymer or lipid with a polynucleotide. Alternatively, the ortho carboxy acetal may be used to crosslink a polymer or lipid after association of the polymer or lipid with a polynucleotide. The ortho carboxy acetal may also be used to attach a functional group to a polynucleotide/delivery agent complex.

A variety of groups can be attached to an ortho carboxy phenol derived acetal. These groups may be selected from the group comprising: polynucleotide, biologically active compound, targeting moiety, ligand, interaction modifier, polycation, polymer, polymer monomer, membrane active compound, hydrophobic group, detergent, and lipid.

In a preferred embodiment, we describe labile crosslinking agents comprising: ortho carboxy acetal dialdehydes. In one embodiment, the dialdehydes may be used to link amines via a pH sensitive linkage. In this way, the dialdehydes may be used to reversibly crosslink amines present in polynucleotide/polyamine complexes, thus stabilizing the complexes. In another embodiment, the dialdehydes may be used as an acid-labile building block to synthesize lipids, polymers, and/or crosslinking reagents that may be useful in the delivery of biologically active compounds.

Further objects, features, and advantages of the invention will be apparent from the following detailed description when taken in conjunction with the accompanying drawings.

DETAILED DESCRIPTION

The present invention relates to the delivery of biologically active compounds to cells using pH-labile linkages and compounds incorporating these pH-labile linkages. The present invention provides compositions and methods for delivery and release of a compound of interest to a cell.

Figure 1:
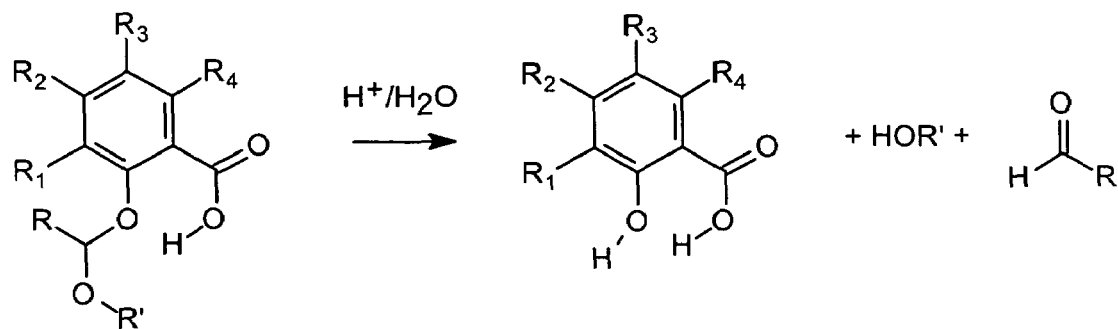
FIG. 1. Illustration of an ortho carboxy acetal and the acid cleavage of an ortho carboxy acetal linkage. R, $R_{1-4}$ can be hydrogen, any carbon-containing group (including, but not limited to any alkyl, aryl, or acyl group) or a heteroatom. R' may be any carbon-containing group (including, but not limited to any alkyl, aryl, or acyl group) or a heteroatom but not hydrogen FIG. 2. Illustration of the structure or three exemplary ortho carboxy acetals used to test cleavage rates. 1. R', R=alkyl; and $R_1$, $R_2$, $R_3$, $R_4$=hydrogen. 2. R', R=alkyl; $R_1$, hydrogen; $R_2$=carboxyl (carbon-containing group); $R_3$=hydroxyl (heteroatom). 3. R'=alkyl; R, $R_2$, $R_3$, $R_4$=hydrogen; and $R_1$=carboxyl (carbon-containing group)

It has been shown that acid groups near an acetal group can facilitate cleavage of the acetal. In particular, ortho carboxy substituted acetals derived from ortho carboxy phenols hydrolyze $10^5$-$10^6$ times faster than the corresponding acetals without ortho carboxy substitution (Fife et al. 1971). The protonated carboxylate accelerates the hydrolysis of the acetal and the carboxylate group is key to rapid hydrolysis kinetics. The corresponding acetals with ortho-substituted ester groups are approximately 22-fold slower in their hydrolysis kinetics (Dunn et al. 1970) The acid cleavage of an ortho carboxy substituted acetal derived from ortho carboxy phenol, is shown in FIG. 1. In an ortho carboxy substituted acetal, R, $R_{1-4}$ can be hydrogen, any carbon-containing group (including, but not limited to any alkyl, aryl, or acyl group) or a heteroatom and R' may be any carbon-containing group (including, but not limited to any alkyl, aryl, or acyl group) or a heteroatom but not hydrogen.

Therefore, to covalently link two compounds via a rapidly hydrolyzed bond, one of the compounds is R or R' and the other is R or $R_{1-4}$. For example, if one compound is R, the other compound may be R' or $R_1$, $R_2$, $R_3$ or $R_4$. If one compound is R', the other compound may be R or $R_1$, $R_2$, $R_3$ or $R_4$. If one compound is $R_1$, $R_2$, $R_3$ or $R_4$, the other compound may be R R'. Similarly, to link three compounds by rapidly hydrolyzed bonds, one of the compounds is R, a second compound is R' and a third compound is $R_1$, $R_2$, $R_3$ or $R_4$. The compounds attached to the acetal may be selected from the group comprising: biologically active compounds, polynucleotides, pharmaceutical agents, peptides, proteins, membrane active compounds, polymers, polymer monomers, transfection agents, lipids, detergents, targeting moieties, and interaction modifiers.

Figure 2:
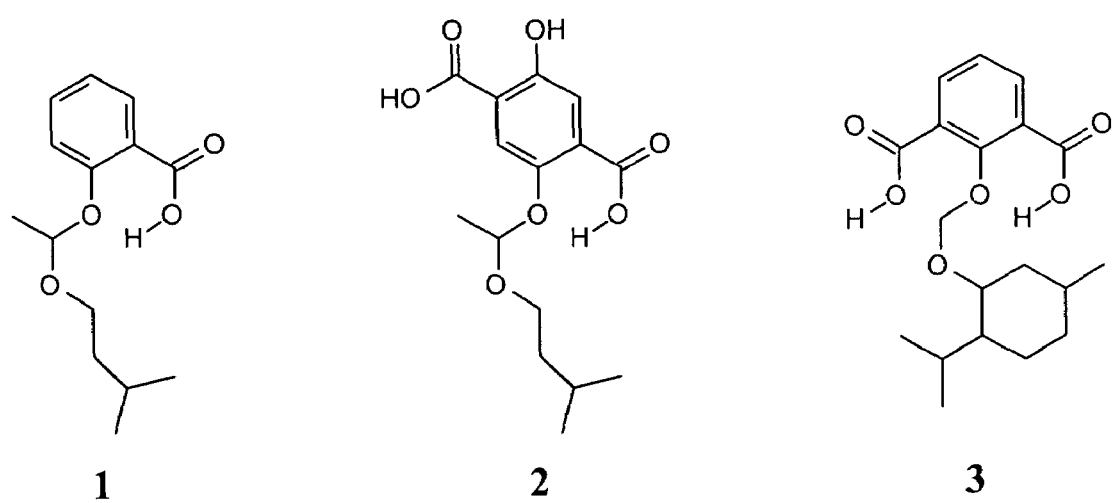

To illustrate the rate of cleavage of several example ortho carboxy phenol derived acetals, we synthesized the molecules 1-3 (shown in FIG. 2) and measured the rates of acetal hydrolysis for each at pH 5.2-7.3.

Acetal 1. R', R=alkyl; and $R_1$, $R_2$, $R_3$, $R_4$=hydrogen

Acetal 2. R', R=alkyl; $R_1$, $R_4$=hydrogen; $R_2$=carboxyl (carbon-containing group); $R_3$=hydroxyl (heteroatom)

Acetal 3. R'=alkyl; R, $R_2$, $R_3$, $R_4$=hydrogen; and $R_1$=carboxyl (carbon-containing group)

| Cleavage rates measured for ortho carboxy phenol derived acetals 1-3 | | |
|---|---|---|
| ACETAL | pH | half-life (minutes) |
| 1 | 7.3 | 1.0 |
| 2 | 7.0 | 1.0 |
| 3 | 6.5 | 4.7 |
| 3 | 5.2 | 0.22 |

The rate of acetal hydrolysis is dependent upon several critical characteristics of the ortho-substituted phenol-derived acetal structures including the aldehyde and the phenol from which the acetal is derived. In particular, acetals derived from formaldehyde (acetal 3) hydrolyze more slowly than acetals derived from alkyl-substituted aldehydes such as acetaldehyde (acetals 1 and 2). Also, substitution of the phenol with another ortho carboxy groups increases the rate above that observed for the monocarboxylate (Dunn et al. 1970).

As can be seen by half-lives of the ortho carboxy phenol derived acetals, the rate of cleavage is rapid at pH 4-7.5. The lability of these acetals allows their use in the construction of agents that disassemble under physiological conditions to aid in drug delivery.

Figure 3:
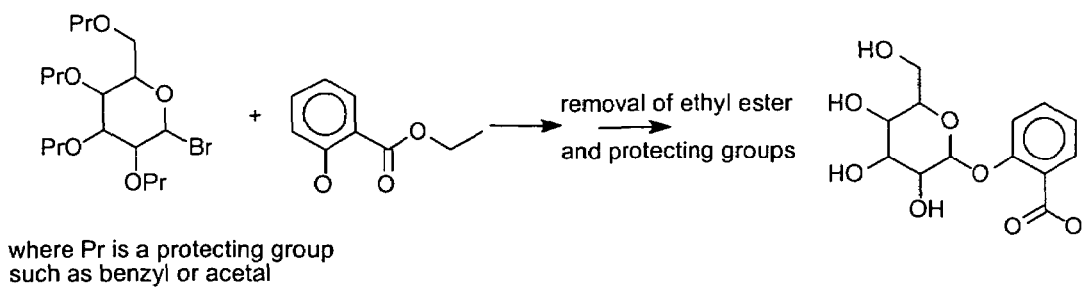
FIG. 3. Illustration of synthesis of a salicylic galactoside, an ortho carboxy phenol-derived acetal.

Saccharides are a well-known class of acetals which have established routes of synthesis. In particular, reaction of 1-bromo protected sugars with ortho carboxy derived phenolates, followed by deprotection, results in a salicylic galactoside, an ortho carboxy phenol derived acetal (FIG. 3; Capon 1963). For this ortho carboxy acetal, R and R' are linked to make the sugar.

Compounds containing multiple aldehyde groups, e.g. glutaraldehyde groups (Adami et al. 1999), are capable of efficient crosslinking. A simple method for synthesizing dialdehydes is the oxidation of cyclic compounds containing vicinal alcohol groups, such as on sugars, by sodium periodate. In particular, sugars with ortho carboxy derived phenolates may be oxidized to produce dialdehydes (see FIG. 4). The dialdehyde may be added to a polyamine-containing particle to crosslink (i.e., cage) the polyamine, thereby stabilizing the particle. Alternatively, the dialdehyde may be used as an acid-labile building block to synthesize lipids, polymers, and/or crosslinking reagents that may be useful in delivery of biologically active compounds.

Ortho carboxy phenol derived acetals may be incorporated into polynucleotide (or other biologically active compound) delivery complexes. Many different molecules can be attached to ortho carboxy phenol derived acetals, at positions R, R', and $R_{1-4}$. Biologically active compounds and a variety of functional groups may be attached to the acetal. The acetal may also be used in the construction on polymers useful for biologically active compound delivery to cells. A plurality of ortho carboxy phenol derived acetals can be incorporated into a polymer to facilitate release of side groups from the polymer or to facilitate cleavage of the polymer backbone.

A polymer can also be designed such that its presence in an endosome prevents acidification of the endosome or facilitates disruption of the endosomal membrane. For example, the polymer can contain endosomolytic properties or have endosomolytic agents or membrane fusion agents attached to it.

The labile acetal bonds described herein may be incorporated into systems that are amphipathic and increase in hydrophobicity and membrane activity upon bond cleavage. For example, the acetal may contain acetals derived from ortho carboxylate phenols having a hydrophilic, negative charge. Cleavage of the acetal separates $R_{1-4}$ from R and R', which removes the link between R and R' and the carboxylate group of the ortho-substituted carboxy phenol. This loss of associated charge may make R and/or R' more hydrophobic, and therefore more likely to interact with and lyse a membrane. Using this strategy one may use acetals derived from ortho carboxylate phenol to construct lipids (where R and R' are long chain, C>10, alkyl groups), or detergents (where R or R' are long chain, C>10, alkyl groups) that become membrane active upon hydrolysis.

Functional groups include cell targeting signals, nuclear localization signals, compounds that enhance release of contents from endosomes or other intracellular vesicles (releasing signals), membrane active compounds, lipids, charged groups, polymers and polymer monomers, transfection enhancing agents, and other compounds that alter the behavior or interactions of the compound or complex to which they are attached. Charged groups include cationic groups which may be used to ionically interact with nucleic acid.

The present invention provides compositions of matter and methods for facilitating the delivery of biologically active compounds to the cells. For the purposes of this invention, the term biologically active compound is intended to encompass all naturally-occurring or synthetic compounds capable of eliciting a biological response or having an effect on biological systems, particularly cells and cellular organelles. A biologically active compound typically has some specific and intended pharmaceutical or biological action. The term thus means any substance intended for use in the diagnosis, cure, mitigation, treatment or prevention of disease or in the enhancement of desirable physical or mental development and conditions in a cell or tissue. The cell may be in vivo or in vitro. Biologically active compounds include, but are not limited to: pharmaceuticals, proteins, peptides, polypeptides, proteins, enzymes, enzyme inhibitors, hormones, cytokines, antigens, viruses, and polynucleotides. The term biologically active compound includes therapeutic agents that provide a therapeutically desirable effect when administered to an animal (e.g., a mammal, such as a human, see Physicians' Desk Reference, 58 ed., 2004, Medical Economics Company, Inc., Montvale, N.J., pages 201-202).

For polynucleotide delivery, it is desirable for the polynucleotide to be dissociated from components of the complex in the cell in order for the polynucleotide to be active. This dissociation may occur outside the cell, within cytoplasmic vesicles or organelles (i.e. endosomes), in the cytoplasm, or in the nucleus. The disclosed acetal linkages can be utilized in forming cleavable components of polynucleotide delivery complexes to facilitate this dissociation of the polynucleotide.

The described acetals and acetal-containing compounds can be used with a variety of delivery routes, including: intravascular (intravenous, intra-arterial), intramuscular, intraparenchymal, intradermal, subdermal, subcutaneous, intratumor, intraperitoneal, intralymphatic, transdermal, oral, nasal, respiratory, and mucosal routes of administration.

Targeting moieties are used for targeting a compound or composition to cells, to specific cells, to tissues or to specific locations in a cell. Targeting moieties enhance the association of compounds or compositions with a cell. The moiety may increase binding of the compound to the cell surface and/or its association with an intracellular compartment. By modifying the cell or tissue localization of a compound, the function of the compound can be enhanced. The targeting moieties can be, but is not limited to, a protein, peptide, lipid, steroid, sugar, carbohydrate, or synthetic compound. Targeting moieties such as ligands enhance binding to cellular receptors. A variety of ligands have been used to target drugs and genes to cells and to specific cellular receptors. The ligand may have affinity for a target within the cell membrane, on the cell membrane or near a cell. Binding of ligands to receptors typically initiates endocytosis. Ligands include agents that target the asialoglycoprotein receptor by using asialoglycoprotein or galactose residues. Other moieties such as insulin, EGF, RGD-containing peptides, folate and other vitamins, and transferrin are other examples of cell receptor targeting ligands. Chemical groups that react with thiols or disulfide groups on cells can also be used to target many types of cells. Other targeting groups include molecules that interact with membranes such as lipids, fatty acids, cholesterol, dansyl compounds, and amphotericin derivatives. In addition viral proteins could be used to bind cells.

After interaction of a compound or complex with the cell, other targeting groups can be used to increase the delivery of the biologically active compound to certain parts of the cell. For example, nuclear localizing signals enhance delivery into proximity of the nucleus and/or entry into the nucleus. Nuclear transport signals can be proteins or peptides, such as the SV40 large T antigen NLS or the nucleoplasmin NLS, that interact with the nuclear transport machinery in the cell. Nuclear transport signals can also be proteins that make up the nuclear transport machinery. For example, karyopherin beta can be used to target compounds the nuclear pore complex.

Membrane active polymers or compounds are molecules that are able to alter membrane structure. This change in structure can be shown by the compound inducing one or more of the following effects upon a membrane: an alteration that allows small molecule permeability, pore formation in the membrane, a fusion and/or fission of membranes, an alteration that allows large molecule permeability, or a dissolving of the membrane. This alteration can be functionally defined by the compound's activity in at least one the following assays: red blood cell lysis (hemolysis), liposome leakage, liposome fusion, cell fusion, cell lysis and endosomal release. More specifically membrane active compounds allow for the transport of molecules with molecular weight greater than 50 atomic mass units to cross a membrane. This transport may be accomplished by either the total loss of membrane structure, the formation of holes (or pores) in the membrane structure, or the assisted transport of compound through the membrane. Membrane active compounds can enhance the release of endocytosed material from intracellular membrane enclosed vesicles. Release includes movement out of an intracellular compartment into the cytoplasm or into an organelle such as the nucleus. Chemicals such as chloroquine, bafilomycin or Brefeldin A1, viruses and viral components such as influenza virus hemagglutinin subunit HA-2 peptides, and other types of amphipathic peptides such as melittin are examples of molecules which have been shown to enhance release of endosomal contents.

An interaction modifier changes the way that a molecule interacts with itself or other molecules relative to molecule containing no interaction modifier. The result of this modification is that self-interactions or interactions with other molecules are either increased or decreased. Steric stabilizers are hydrophilic polymers that decrease electrostatic interactions between molecules and themselves and with other molecules. Steric stabilizers such as polyethylene glycol have been used to reduce interactions with blood components to increase circulatory time of a compound or composition to which they are attached by preventing opsonization, phagocytosis and uptake by the reticuloendothelial system. Other steric stabilizers include: alkyl groups, and polysaccharides.

A transfection agent, or transfection reagent or delivery vehicle, is a compound or compounds that bind(s) to or complex(es) with oligonucleotides and polynucleotides, and mediates their entry into cells. Examples of transfection reagents include, but are not limited to, cationic liposomes and lipids, polyamines, calcium phosphate precipitates, histone proteins, polyethylenimine, polylysine, and polyampholyte complexes. It has been shown that cationic proteins like histones and protamines, or synthetic polymers like polylysine, polyarginine, polyornithine, DEAE dextran, polybrene, and polyethylenimine may be effective intracellular delivery agents. Typically, the transfection reagent has a component with a net positive charge that binds to the oligonucleotide's or polynucleotide's negative charge. The transfection reagent mediates binding of oligonucleotides and polynucleotides to cells via its positive charge (that binds to the cell membrane's negative charge) or via ligands that bind to receptors in the cell. For example, cationic liposomes or polylysine complexes have net positive charges that enable them to bind to DNA or RNA. For non-viral delivery, polynucleotides can be incorporated into lipid vesicles (liposomes), complexed with polymers (polyplexes) or a combination of lipids and polymers (lipopolyplexes).

Amphiphilic, or amphipathic, compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bonds. Hydrocarbons are hydrophobic groups.

Detergents or surfactants are water-soluble molecules containing a hydrophobic portion (tail) and a hydrophilic portion (head), which upon addition to water decrease water's surface tension. The hydrophobic portion can be alkyl, alkenyl, alkynyl or aromatic. The hydrophilic portion can be charged with either net positive (cationic detergents), negative (anionic detergents), uncharged (nonionic detergents), or charge neutral (zwitterionic detergent). Examples of anionic detergents are sodium dodecyl sulfate, glycolic acid ethoxylate (4 units) 4-tert-butylphenylether, palmitic acid, and oleic acid. Examples of cationic detergents are cetyltrimethylammonium bromide and oleylamine. Examples of nonionic detergents include, laurylmaltoside, Triton X-100, and Tween. Examples of zwitterionic detergents include 3-[(3-cholamidopropyl)dimthylammonio]1-propane-sulfonate (CHAPS), and N-tetradecyl-N,N-dimethyl-3-ammoniu-1-propanesulfonate.

A polymer is a molecule built up by repetitive bonding together of smaller units called monomers. A polymer can be linear, branched network, star, comb, or ladder types of polymer. A polymer can be a homopolymer in which a single monomer is used or can be copolymer in which two or more monomers are used.

The main chain of a polymer is composed of the atoms whose bonds are required for propagation of polymer length. For example in poly-L-lysine, the carbonyl carbon, α-carbon, and α-amine groups are required for the length of the polymer and are therefore main chain atoms. The side chain of a polymer is composed of the atoms whose bonds are not required for propagation of polymer length. For example in poly-L-lysine, the β, γ, δ and ε-carbons, and ε-nitrogen are not required for the propagation of the polymer and are therefore side chain atoms.

Other Components of the Monomers and Polymers: Polymers may have functional groups that enhance their utility. These groups can be incorporated into monomers prior to polymer formation or attached to the polymer after its formation. Functional groups may be selected from the list consisting of: targeting groups, interaction modifiers, steric stabilizers, and membrane active compounds, affinity groups and reactive groups.

A polyion (or polyelectrolyte), is a polymer possessing charge, i.e. the polymer contains a group (or groups) that has either gained or lost one or more electrons. The term polyion includes polycations, polyanions, zwitterionic polymers, and neutral polymers. The term zwitterionic refers to the product (salt) of the reaction between an acidic group and a basic group that are part of the same molecule. Salts are ionic compounds that dissociate into cations and anions when dissolved in solution. Salts increase the ionic strength of a solution, and consequently decrease interactions between nucleic acids with other cations. A charged polymer is a polymer that contains residues, monomers, groups, or parts with a positive or negative charge and whose net charge can be neutral, positive, or negative.

A polycation can be a polymer possessing net positive charge, for example poly-L-lysine hydrobromide or a histone. The polymeric polycation can contain monomer units that are charge positive, charge neutral, or charge negative, however, the net charge of the polymer must be positive. A polycation also can be a non-polymeric molecule that contains two or more positive charges.

A polyanion can be a polymer containing a net negative charge, for example polyglutamic acid. The polymeric polyanion can contain monomer units that are charge negative, charge neutral, or charge positive, however, the net charge on the polymer must be negative. A polyanion can also be a non-polymeric molecule that contains two or more negative charges.

A labile bond is a covalent bond that is capable of being selectively broken. That is, the labile bond may be broken in the presence of other covalent bonds without the breakage of the other covalent bonds. For example, a disulfide bond is capable of being broken in the presence of thiols without cleavage of any other bonds, such as carbon-carbon, carbon-oxygen, carbon-sulfur, carbon-nitrogen bonds, which may also be present in the molecule.

pH-labile refers to the selective breakage of a covalent bond under acidic conditions (pH<7). That is, the pH-labile bond may be broken under acidic conditions in the presence of other covalent bonds without their breakage.

The term polynucleotide, or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides. The term base encompasses any of the known base analogs of DNA and RNA. The term polynucleotide includes deoxyribonucleic acid (DNA) and ribonucleic acid (RNA) and combinations of DNA, RNA and other natural and synthetic nucleotides.

A polynucleotide can be delivered to a cell to express an exogenous nucleotide sequence, to inhibit, eliminate, augment, or alter expression of an endogenous nucleotide sequence, or to affect a specific physiological characteristic not naturally associated with the cell. Polynucleotides can be delivered to cells to treat genetic disorders, treat acquired diseases such as cancer, induce an immune reaction (such as in vaccination or immunization), treat infectious disorders, add a new cellular function, or study gene function.

A polynucleotide-based gene expression inhibitor comprises any polynucleotide containing a sequence whose presence or expression in a cell causes the degradation of or inhibits the function, transcription, or translation of a gene in a sequence-specific manner.

Polynucleotide-based expression inhibitors may be selected from the group comprising: siRNA, microRNA (miRNA), small non-messenger RNAs (snmRNA), utRNA (untranslated), snoRNAs (24-mers, modified snmRNA that act by an anti-sense mechanism), tiny non-coding RNAs (tncRNAs), interfering RNA or RNAi, dsRNA, ribozymes, antisense polynucleotides, and DNA expression cassettes encoding the like. SiRNA comprises a double stranded structure typically containing 15-50 base pairs and preferably 19-25 base pairs and having a nucleotide sequence identical or nearly identical to an expressed target gene or RNA within the cell. An siRNA may be composed of two annealed polynucleotides or a single polynucleotide that forms a hairpin structure (small hairpin RNA, shRNA). MicroRNAs are small noncoding polynucleotides, about 22 nucleotides long, that direct destruction or translational repression of their mRNA targets. Antisense polynucleotides comprise sequence that is complimentary to a gene or mRNA. Antisense polynucleotides include, but are not limited to: morpholinos, 2'-O-methyl polynucleotides, DNA, RNA and the like. The polynucleotide-based expression inhibitor may be polymerized in vitro, recombinant, contain chimeric sequences, or derivatives of these groups. The polynucleotide-based expression inhibitor may contain ribonucleotides, deoxyribonucleotides, synthetic nucleotides, or any suitable combination such that the target RNA and/or gene is inhibited.

The process of delivering a polynucleotide to a cell has been commonly termed transfection or the process of transfecting and also it has been termed transformation. The term transfecting as used herein refers to the introduction of a polynucleotide or other biologically active compound into cells. The polynucleotide may be used for research purposes or to produce a change in a cell that can be therapeutic. The delivery of a polynucleotide for therapeutic purposes is commonly called gene therapy. The delivery of a polynucleotide can lead to modification of the genetic material present in the target cell. The term stable transfection or stably transfected generally refers to the introduction and integration of an exogenous polynucleotide into the genome of the transfected cell. The term stable transfectant refers to a cell which has stably integrated the polynucleotide into the genomic DNA. Stable transfection can also be obtained by using episomal vectors that are replicated during the eukaryotic cell division (e.g., plasmid DNA vectors containing a papilloma virus origin of replication, artificial chromosomes). The term transient transfection or transiently transfected refers to the introduction of a polynucleotide into a cell where the polynucleotide does not integrate into the genome of the transfected cell. If the polynucleotide contains an expressible gene, then the expression cassette is subject to the regulatory controls that govern the expression of endogenous genes in the chromosomes. The term transient transfectant refers to a cell which has taken up a polynucleotide but has not integrated the polynucleotide into its genomic DNA.

EXAMPLES

Example 1

Synthesis of Model Acetals 1-2

To a solution of 100 mg of isoamyl alcohol and 55 mg (1.1 eq) of acetaldehyde in 2 mL of anhydrous methylene chloride at 4° C. was added 200 mg of hydrochloric acid. The reaction was sealed with a rubber septum and stirred at RT for 24 hours. The solvent was then removed by rotary evaporation to produce the chloroether as a clear oil.

The phenolate anion of ethyl salicylate (for acetal 1; FIG. 1) and diethyl 2,5-dihydroxyterephthalate (for acetal 2; FIG. 1) were generated by addition of phenol to 0.9 equivalents of sodium hydride in anhydrous dimethylformamide. To the phenolate was then added 1.1 equivalents of the isoamyl-acetaldehyde chloroether. After 24 hours at room temperature (RT), the reaction was partitioned between water and ethyl acetate. The ethyl acetate was isolated, dried with sodium sulfate and concentrated to a solid.

The ester groups were then removed by addition of 2 equivalents of potassium hydroxide in methanol. After 3 hours, the ortho carboxy phenolate acetal was purified by reverse phase HPLC using a $C_{18}$ column using methanol and water containing 0.1 wt % ammonium carbonate as eluents.

Example 2

Synthesis of Model Acetal 3

Synthesis of dimethyl-2-hydroxyisophthalic acid: 200 mg of 2-methoxyisophthalic acid was placed in a screw cap vial with 1.1 equivalents of sodium iodide and 10 mL of hydrogen bromide solution (48%). The vial was sealed and heated to 100° C. in a water bath for 2 hours. The white precipitate was isolated by centrifugation and washed with dilute aqueous hydrochloric acid solution. The methyl diester was synthesized by reaction with methanol (100 mL) and concentrated sulfuric acid (10 mL) refluxing for 3 hours. The methanol was then removed by rotary evaporation and the mixture was partitioned between water and ethyl acetate. The organic layer was isolated, dried with sodium sulfate and concentrated to a white solid, which was purified by silica gel chromatography eluting with a hexane/ethyl acetate gradient.

Acetal 3 (FIG. 1) was synthesized by alkylation of chloromethyl menthol (0.5 equivalent from Aldrich) in dimethylformamide using sodium hydride (1 equivalent) as a base. The diester acetal was converted to diacid acetal by 5 eq potassium hydroxide in methanol. After 3 hours, the ortho carboxy phenolate acetal 3 was purified by reverse phase HPLC using a $C_{18}$ column using methanol and water containing 0.1 wt % ammonium carbonate as eluents.

Example 3

Measurement of Acetal Kinetics

To determine the rate of acetal hydrolysis, compounds 1-3 were added to buffered solutions (pH 7-8 with 5 mM HEPES, or pH 5-7 with 5 mM acetate) at various pH values and the absorbance of the solution was measured as a function of time ($\lambda$=302 nm for 1 and 2 and 310 nm for 3). The rate constant was determined by determining the slope of the line derived from plotting $\ln[1-((A_\infty-A_t)/(A_{28}-A_o))]$ as a function of time t, where $A_{28}$ is absorbance after >3 hours of hydrolysis, $A_t$ is the absorbance at time t, and $A_o$ is the initial absorbance. The half-life of the hydrolysis equals ln[2] divided by the rate constant.

Example 4

Synthesis of Galactose-Salicylate

The sodium phenolate of ethyl salicylic acid was generated by 1 equivalent of sodium hydride in dimethylformamide. To the phenolate was added acetobromo-β-D-galactose (Sigma). The solution was stirred at RT for 10 days. The reaction mixture was partitioned between ethyl acetate and water, and the product was isolated by silica gel chromatography elution with hexane/ethyl acetate (see FIG. 3).

Example 5

Removal of Ester Groups and Oxidation of Galactose-Salicylate

Figure 4:
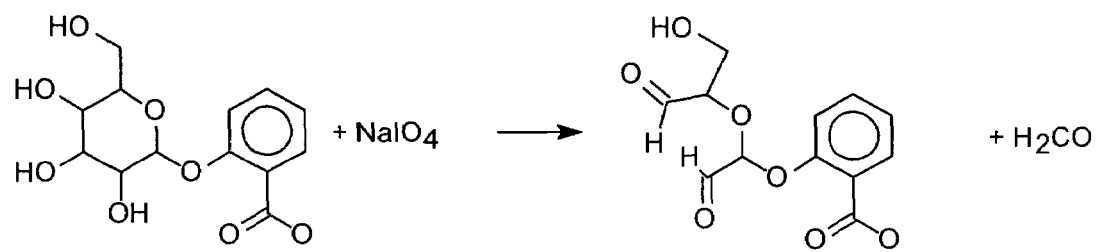
FIG. 4. Illustration of oxidation of sugars with ortho carboxy derived phenolates to produce dialdehydes.

To a solution of ester galactose-salicylate in methanol was added 1 vol equivalent of water and 10 equivalents of potassium hydroxide. To this solution was added 5 equivalents of sodium periodate (FIG. 4).

Example 6

Synthesis of Polycation DW561 and DW921

2-Vinyloxy Ethyl Phthalimide (1 g, 4.6 mmol) was added to an oven dried round bottom flask under a blanket of nitrogen in anhydrous dichloromethane. To this solution was added butyl vinyl ether (0.368 g 3.68 mmol (DW921), or 0.460 g, 4.6 mmol (DW561)). The solution was then brought to −78° C. and $BF_3.OEt_2$ (0.065 g, 0.46 mmol) is added and the reaction is allowed to proceed for 2 hours at −78° C. The polymerization was stopped by the addition of 50/50 mixture of ammonium hydroxide in methanol. The solvents were then removed by rotary evaporation. The polymer was then dissolved in 30 mL of 1,4-dioxane/methanol (2:1). To this solution was added hydrazine (0.147 g, 46 mmol) and the mixture was heated to reflux for 3 hours. The solvents were then removed by rotary evaporation and the resulting solid was brought up in 20 mL of 0.5M HCl and refluxed for 15 minutes, diluted with 20 mL distilled water, and refluxed for additional hour. This solution was then neutralized with NaOH, cooled to RT, transferred to 3,500 molecular weight cutoff cellulose tubing, dialyzed for 24 h (2×20 L) against distilled water, and freeze dried.

Example 7

PEGylation of DW921

100 mg of purified DW921 was reacted with 20 mg of PEG (3500) NHS ester in 1 mL HEPES pH 7.5. The polymer was then purified by size exclusion chromatography using sephacryl S-200 to remove unreacted PEG.

Example 8

Crosslinking and Decondensation Assay

The condensation of TMR-labeled DNA was assessed using a quantitative assay based on condensation-induced quenching of a fluorophore covalently attached to DNA. Briefly, TMR-DNA (3 μg/mL) was mixed 30 μg/mL DW921 in 0.8 ml of 10 mM HEPES, pH 7.5. After condensation with the polycation, periodate oxidized galactose-salicylate was added to 5 μg/mL. The TMR fluorescence of the samples was then measured using a Cary spectrofluorometer (excitation wavelength ($\lambda_{ex}$) of 555 nm; emission wavelength ($\lambda_{em}$) of 585 nm) at RT. Relative signal was calculated as the percentage of fluorescence of noncondensed TMR-DNA. After 10 minutes, the condensed DNA particle was "challenged" by the addition of sodium chloride to 2.5 M. The level of fluorescence was compared to DNA particles without the addition of galactose-salicylate.

| Sample | fluorescence intensity |
|---|---|
| DNA alone no salt | 457 |
| 2.5 M NaCl | 333 |
| DNA with DW921 | 214 |
| − galactose-salicylate, +2.5 M salt | 276 |
| + galactose salicylate, +2.5 M salt | 232 |

The increase in fluorescence after addition of sodium chloride is due to the decondensation of the DNA as the salt displaces the polycation, and therefore, is a measurement of crosslinking when comparing the noncrosslinked (no galactose-salicylate) to crosslinked samples (with galactose-salicylate).

Example 9

DNA Transfection

To a solution of plasmid DNA pCIluc (10 μg/mL, 0.075 mM in phosphate, 2.6 μg/μL pCIluc; prepared according to Danko et al. 1997) in 0.5 mL of 150 mM NaCl and 5 mM TAPS pH 9 was added 100 μg/mL DW921. The complexes were then reacted with glutaraldehyde, periodate oxidized phenyl glucoside (another crosslinker containing a labile bond), or periodate oxidized salicylic galactoside at 1, 2, 4, 8, or 16 μg/mL. The complexes were then added (200 μL) to wells containing Hepa mouse hepatoma cells in Dulbecco's modified Eagle's Media containing 10% fetal bovine serum. The cells were allowed to incubate for 48 h. The cells were then harvested and assayed for luciferase expression as previously reported. The amount of transfection was reported in relative light units and is the average transfection for two separate wells of cells.

| | Relative Light Units | | |
|---|---|---|---|
| μg/mL dialdehyde crosslinker | glutaraldehyde (non-labile) | periodate oxidized phenyl glucoside | periodate oxidized salicylic galactoside |
| 0 | | 461,140 | |
| 1 | 915 | 367,085 | 408,625 |
| 2 | 620 | 381,135 | 430,545 |
| 4 | 1,400 | 391,215 | 409,665 |
| 8 | 590 | 359,595 | 454,980 |
| 16 | 565 | 310,445 | 359,655 |

These data show that caging (i.e. crosslinking) the DNA-containing particles with a cleavable crosslinker results in better expression of the reporter transgene that caging with a non-hydrolyzable crosslinker.

Example 10

In Vivo DNA Delivery (Mouse)

To a solution of plasmid DNA pCIluc (3.33 µg/mL) in 3 mL of 5 mM TAPS pH 9 was added 33.3 µg/mL DW921. The complexes were then reacted with glutaraldehyde, periodate oxidized phenyl glucoside, or periodate oxidized salicylic galactoside at 1.66, 3.33, or 8.33 µg/mL respectively. The complexes were then injected into the tail vein of 32 g mice using a 27 gauge needle in ≦10 seconds. All mice were euthanized at one day post-injection and livers were collected and homogenized in luciferase assay buffer. Luciferase activity was assayed from each liver homogenate sample (i.e. each mouse) as previously reported (Wolff et al. 1990). The amount of transfection was reported in relative light units and is the average for two mice.

| Relative Light Units | |
|---|---|
| periodate oxidized phenyl glucoside | periodate oxidized salicylic galactoside |
| 171,643 | 151,953 |

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

What is claimed is:

1. An ortho carboxy dialdehyde consisting of a structure represented by:

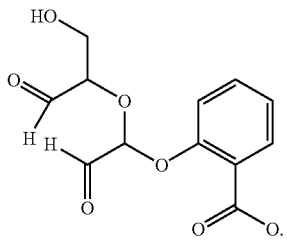

2. A method for forming a labile linkage between amine groups present in one or more compounds comprising:
    a) forming an ortho carboxy acetal dialdehyde represented by the structure:

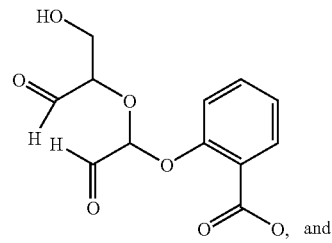

b) reacting said dialdehyde with said amine groups.

3. The method of claim 2 wherein said compound consists of a transfection agent.

4. The method of claim 3 wherein said transfection agent is associated with a polynucleotide.

5. A method for delivering a polynucleotide to a cell comprising:
    a) associating said polynucleotide with an amine-containing transfection agent to form a complex;
    b) adding an ortho carboxy acetal dialdehyde represented by the structure:

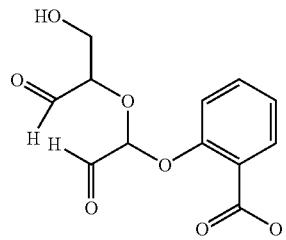

to said complex thereby crosslinking amines of said transfection agent to form a crosslinked complex; and,
    c) associating said crosslinked complex with a cell thereby delivering said polynucleotide to said cell.

6. The method of claim 5 wherein said cell is in vivo.

7. The method of claim 5 wherein said cell is in vitro.

* * * * *